United States Patent [19]

Teves

[11] Patent Number: 5,080,107

[45] Date of Patent: * Jan. 14, 1992

[54] CARDIAC MONITOR WITH ENDOTRACHEAL SENSOR

[76] Inventor: Leonides Y. Teves, 623 39th St. West, Bradenton, Fla. 34205

[*] Notice: The portion of the term of this patent subsequent to Nov. 6, 2007 has been disclaimed.

[21] Appl. No.: 332,919

[22] Filed: Apr. 4, 1989

Related U.S. Application Data

[63] Continuation-in-part of Ser. No. 233,629, Aug. 18, 1988, Pat. No. 4,967,759, which is a continuation-in-part of Ser. No. 213,296, Jun. 29, 1988, abandoned.

[51] Int. Cl.⁵ .................................................. A61B 8/02
[52] U.S. Cl. ..................................... 128/773; 128/670; 128/661.07
[58] Field of Search ............. 128/773, 661.07, 661.08, 128/671, 670, 660.01, 660.02, 662.06

[56] References Cited

U.S. PATENT DOCUMENTS

| | | | |
|---|---|---|---|
| 3,779,234 | 12/1973 | Eggleton et al. | 128/662.06 |
| 4,319,580 | 3/1982 | Colley et al. | 128/661.07 |
| 4,607,643 | 8/1986 | Bell et al. | 128/773 |
| 4,802,490 | 2/1989 | Johnston | 128/661.08 |
| 4,823,812 | 4/1989 | Eshel et al. | 128/784 |
| 4,841,977 | 6/1989 | Griffith et al. | 128/662.06 |

FOREIGN PATENT DOCUMENTS

2424733  1/1980  France ............................ 128/662.06

*Primary Examiner*—William E. Kamm
*Assistant Examiner*—Scott M. Getzow
*Attorney, Agent, or Firm*—Joseph C. Mason, Jr.; Ronald E. Smith

[57] ABSTRACT

An endotracheal tube and inflatable cuff assembly that allows medical instrumentation to be positioned in the trachea. The device remains securely placed in the trachea and allows the passage of gases to the lungs to be controlled. It also provides means for containing various medical instrumentation in a hermetically sealed environment. The device is used during surgery for placement of medical instrumentation, such as heart monitors and electrodes for atrial pacing, inside a hermetically sealed inflatable cuff such that the instrumentation can be appropriately positioned inside the trachea. The device also enables the physician to insert a low pressure gauge, a temperature gauge, an echo probe or other sensing means into the cuff, or to listen directly to acoustical phenomena within the cuff in the absence of instrumentation.

12 Claims, 3 Drawing Sheets

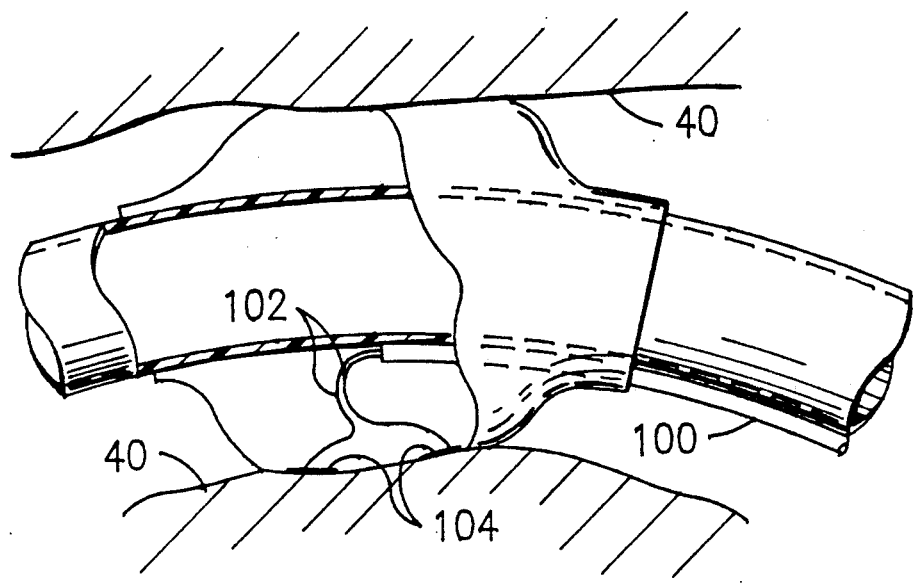
FIG. 4
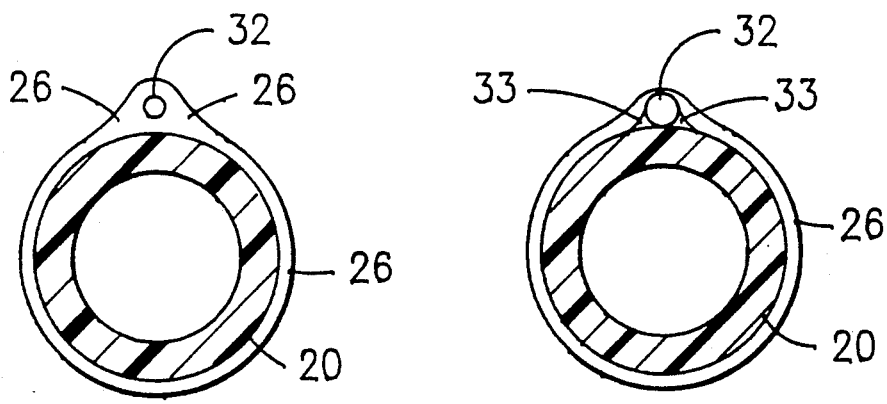
FIG. 6
FIG. 7

CARDIAC MONITOR WITH ENDOTRACHEAL SENSOR

CROSS-REFERENCE TO RELATED APPLICATION

This disclosure is a continuation-in-part of a co-pending disclosure by the same inventor bearing serial number U.S. Ser. No. 07/233,629, now U.S. Pat. No. 4,967,759, filing date Aug. 18, 1988, which disclosure is a continuation-in-part of a co-pending disclosure by the same inventor bearing Ser. No. 07/213,296, now abandoned filing date Jun. 29, 1988, which disclosure is a continuation of a co-pending disclosure by the same inventor bearing serial number. Canadian serial number 539,054, filing date Jun. 8, 1987, all of which disclosures are entitled Cardiac Monitor with Endotracheal Sensor.

TECHNICAL FIELD

This invention relates to endotracheal tubes for medical applications, and more particularly to endotracheal tubes having inflatable cuffs adapted to contain medical instrumentation. Such instrumentation may include electrodes for the purposes of atrial pacing of the heart, and apparatus for acoustically or electronically monitoring the heart.

BACKGROUND ART

During operations in which general anesthesia is used, it is common to administer anesthetic gases through a flexible endotracheal tube which passes through the mouth and into the trachea of the patient. In order to obtain positive control over the patient's breathing and the administration of the anesthesia, it is necessary to block a portion of the trachea exterior to the endotracheal tube. Such blockage should completely seal off passage of air between the distal and proximal ends of the trachea, exterior to the endotracheal tube. This is typically accomplished by using an inflatable cuff hermetically sealed to the tube in proximity to the tube's distal end. The cuff, when inflated, conforms intimately to the wall of the trachea, thus sealing the tracheal passage exterior to the tube.

Because of the relaxed state of the patient, it is necessary to monitor the patient's heart while the patient is under the influence of anesthesia. Monitoring of the heart may consist of simply listening to the heart rate, including electronically monitoring the heart rate with respect to minimum and maximum values. It is preferable, however, to monitor the heart in such a way that the actual sounds made by the various components of the heart may be heard clearly and distinctly. Information pertaining to the state of a patient's condition can be discerned from these sounds by a skilled anesthesiologist. Such information would be used to determine subsequent administration of anesthetic, or to advise the surgeon of the condition of the patient.

In some cases, monitoring is accomplished by external means such as an EKG monitor. Such external means do not provide a proper reproduction of heart sound, however, and therefore are generally unacceptable. Moreover, since EKGs are electromechanical devices, there is a substantial time delay between the onset of a particular heart condition and the recording of such condition by the machine.

It is possible to monitor heart sounds using a sound monitoring means located in the esophagus. An esophageal monitoring means, however, may produce a signal that can be quite noisy due to variations in body fluids in the esophagus during surgery. Another problem is the introduction of a second tube into the mouth, in addition to the endotracheal tube, thus creating undesirable crowding and trauma.

It has been found that endotrachial monitoring of the heart produces the most useful and consistent results. It is possible to hear various characteristic sounds of the heart, and to distinguish them from other extraneous sounds such as breathing. All known forms of endotrachial monitoring devices are pneumatic in nature, and interface with an electro-acoustic sensing device external to the patient's body, through a lumen in the endotracheal tube. This allows breathing sounds to be transmitted via the lumen.

In addition to being able to monitor the heart, it is sometimes required that the heart be artificially stimulated into beating in a rhythmic manner. This artificial electrical stimulation, known as pacing, may be either atrial or ventricular. It has been found, however, that ventricular pacing is used with variable success. Atrial pacing, which has been developed more recently, is generally more successful. Two types of atrial pacing are typically used: direct and esophageal. Direct atrial pacing involves placement of electrodes on the left atrium during open heart surgery. Esophageal atrial pacing involves introduction of a lead into the esophagus such that a pair of electrodes contacts the wall of the esophagus closest to the heart. A series of current pulses is subsequently delivered through these electrodes, thus stimulating the left atrium.

The invention shows some characteristics in common with the prior art shown in U.S. Pat. Nos. 4,263,921 to Trugillo, 4,331,156 to Apple et al., 4,383,534 to Peters, and Canadian patent No. 1,209,213 to Teves.

In Apple et al., an esophageal cardiac pulse probe is disclosed wherein a flexible diaphragm contacts the inner wall of the esophagus. Pressure variations in the diaphragm due to movement in the esophagus are transmitted through a lumen to an external electrical transducer. The lumen is concentric with a larger second lumen, which is used for direct acoustic monitoring.

Peters discloses a device that operates on a principle similar to Apple, but is inserted into the trachea, not the esophagus. Also disclosed are a lumen that is an integral part of the endotracheal tube wall and an EKG sensing device mounted on the exterior of the endotracheal tube at the distal end. Exterior mounting of any device is not desirable since the device could become dislodged from the apparatus. Peters teaches that it is desirable to monitor cardiac sounds from the trachea as opposed to the esophagus due to its proximity to the heart. Moreover, Peters is concerned with monitoring breath sounds together with cardiac monitoring.

Teves distinguishes from Peters by teaching an endotracheal device for monitoring heart sounds only, with different structure that attenuates respiratory sounds reaching the lumen by placing the lumen external to the endotracheal tube. Additionally, Teves discloses an inflatable cuff that is longer and more pliant that other cuffs, which reduces irritation of the trachea inner wall.

Trugillo discloses an endotracheal tube and inflatable cuff apparatus that has a temperature sensing means embedded in the wall of the tube adjacent to the proximal end of the cuff. This configuration solves the possible problem of dislodging inherent in Peters. The wires associated with the temperature sensing device are located in a lumen in the wall of the tube. However, Trugillo does not address the problem of endotracheal monitoring using any kind of sensor means within the cuff.

DISCLOSURE OF INVENTION

The present invention comprises an apparatus which permits the administration of anesthetic gases to a patient during surgery through an endotracheal tube, and which also permits internal placement of various devices. Such devices are to be used for either monitoring of the patient's heartbeat, or to perform atrial pacing, from inside the trachea. During surgery, an endotracheal tube apparatus is placed in the trachea for the purposes of administering anesthesia and the present invention would allow this already present apparatus to be used for placement of a sensing device.

It is advantageous to monitor or pace the heart from the trachea since the trachea is juxtaposed to the left atrium. It is therefore possible to obtain high quality auditory signals representing the various sounds of the heart. It is also possible to perform atrial pacing using lower current electrical pulses than would be used in esophageal atrial pacing.

The present invention provides means for monitoring the heart using an acoustic monitoring device located inside the cuff of the endotracheal tube. The omission of sound transmission by pneumatics greatly reduces the amount of breathing sounds that are picked up. Additionally, it is possible to place a pair of electrodes in the cuff for the purpose of atrial pacing. Due to the close proximity of the trachea to the left atrium, tracheal atrial pacing produces more consistent results than does esophageal atrial pacing.

An important object of the invention is to provide an endotracheal tube means having at least a secondary tube of smaller diameter that transmits information to the attending anesthesiologist of a patient in surgery.

The invention accordingly comprises the features of construction, combination of elements and arrangement of parts that will be exemplified in the descriptions set forth hereinafter and the scope of the invention will be set forth in the claims.

BRIEF DESCRIPTION OF DRAWINGS

For a fuller understanding of the nature and objects of the invention, reference should be made to the following detailed description, taken in connection with the accompanying drawings, in which:

FIG. 4 is an enlarged partially cut away and sectional view of the endotracheal tube and inflatable cuff similar to FIG. 2, and includes an installed electrode means for atrial pacing;

FIG. 6 is a transverse sectional view taken along line 6—6 in FIG. 1; and

FIG. 7 is a transverse sectional view of an alternative embodiment of the invention.

Similar reference numerals refer to similar parts throughout the several views of the drawings.

BEST MODES FOR CARRYING OUT THE INVENTION

Figure 1:
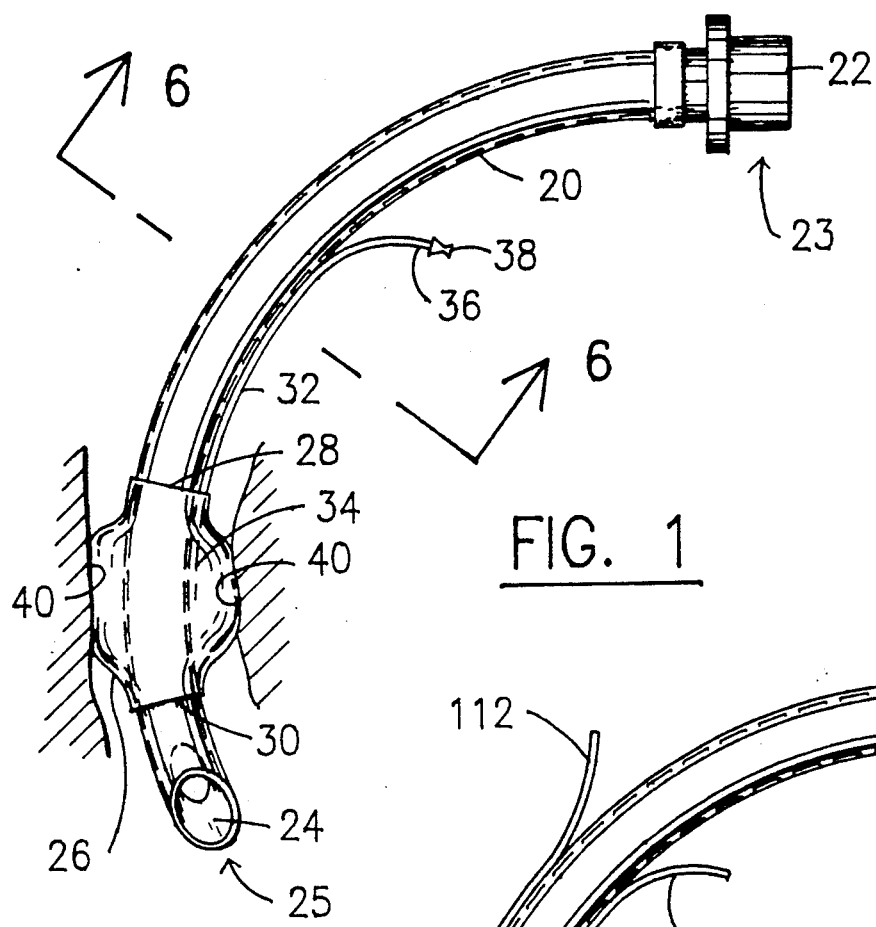
FIG. 1 is a side view, partially in cross section, of the novel endotracheal tube showing the cuff inflated within the trachea.

FIG. 1 is a side view of the endotracheal tube and inflatable cuff apparatus, partially in cross-section, when inserted into the trachea of a patient. The long hollow tube 20 starts at the proximal end 23, where it is attached to the external coupling 22 and continues along the trachea where it terminates in an opening 24 in distal end 25. Anesthetic gases are administered to a patient through this tube 20.

An inflatable cuff 26 is attached to the tube 20 near its distal end. Cuff 26 is hermetically sealed to the tube 20 at both its proximal end 28 and distal end 30. The interior of inflatable cuff 26 is thus sealed off to the exterior and can be accessed only through lumen 32.

The lumen 32 run is substantially parallel to the tube 20 and it may be formed as an integral part thereof as perhaps best shown in FIG. 6. Alternatively, lumen 32 may be independently formed and secured to the tube 20 by suitable adhesive means such as tape means 33 as shown in FIG. 7.

As shown in FIG. 1, the distal end 34 of the lumen 32 is open to the interior of the inflatable cuff 26. The proximal end 36 of the lumen 32 is adapted to interface with means for inflating the cuff 26, by use of a coupling means 38. The preferred inner diameter of the lumen 32 is at least 1.0 mm.

When cuff 26 is inflated, its outer surface comes in intimate contact with the walls of the trachea 40. The cuff 26, in its inflated state, is used to block off the trachea and thus preclude air or other gases from passing through the trachea and into the lungs, except for the controlled flow of anesthetic gases through hollow tube 20. In order to insert the tube 20 and the inflatable cuff 26 into the trachea, or to remove them therefrom, the cuff must be in a deflated state.

The operation of the apparatus according to this invention is now discussed with reference to FIG. 2, in which the apparatus is configured as an acoustic endotracheal heart monitor. The hollow tube 20 and inflatable cuff 26 are shown in a position similar as that shown in FIG. 1. Depending from the distal end 34 of lumen 32 is a sound pressure level sensing means 42, which is acoustic in nature. A pair of thin wires 44 are functionally attached to the sensing means 42. The wires 44 enter lumen 32 at its distal end 34 and continue along the entire length of the lumen 32 and extend outwardly to the exterior of the apparatus. These wires 44 provide means for sending electrical signals generated by the sound pressure level sensing means 42 to an external monitor.

Sensing means 42 is retained in fixed relation inside the cuff 26 by a base element 45 that is fastened to the outer wall of the tube 20. The base element 45 is preferably constructed of a material that minimizes the amount of vibration transmitted from the hollow tube 20 to the sensing means 42.

After the inflatable cuff 26 has been properly positioned in the trachea, it is inflated through lumen 32.

When proper inflation is realized, the proximal end 36 of the lumen 32 is removed from the inflating source. The coupling means 38, containing a check valve, prevents the cuff from deflating. The internal air pressure should be about 1 p.s.i. greater than the external air pressure surrounding the cuff (1 p.s.i.g.). The wall of the cuff is acoustically transparent, so that heartbeat sounds travelling in the chest cavity and into the trachea are transmitted through the cuff walls to the interior of the cuff, and are represented by changes in sound level pressure within the cuff. This change in sound pressure level is sensed by sound pressure level means 42, which produces a corresponding electrical signal to be transmitted through wires 44. By this method, an accurate representation of the sound of the heartbeat can be received by an external monitor.

Another embodiment, not shown in the drawings, includes a sound pressure level sensing means used in conjunction with a self-contained radio frequency emitting device. It is contemplated that these sending means and any transmitting device could be one integral unit.

Figure 2:
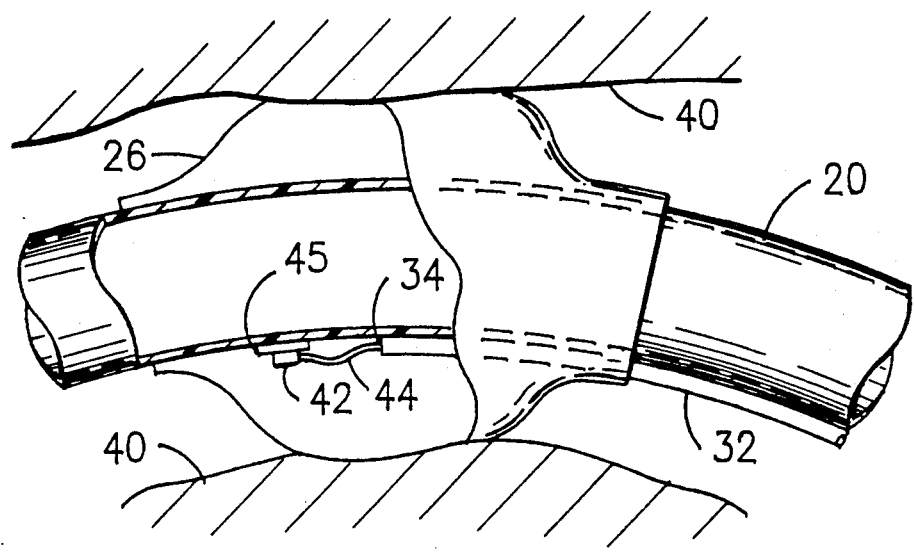
FIG. 2 is an enlarged partially cut away sectional view of the endotracheal tube and inflatable cuff depicted in FIG. 1 and includes an installed sound pressure level sensing means.
Figure 3:
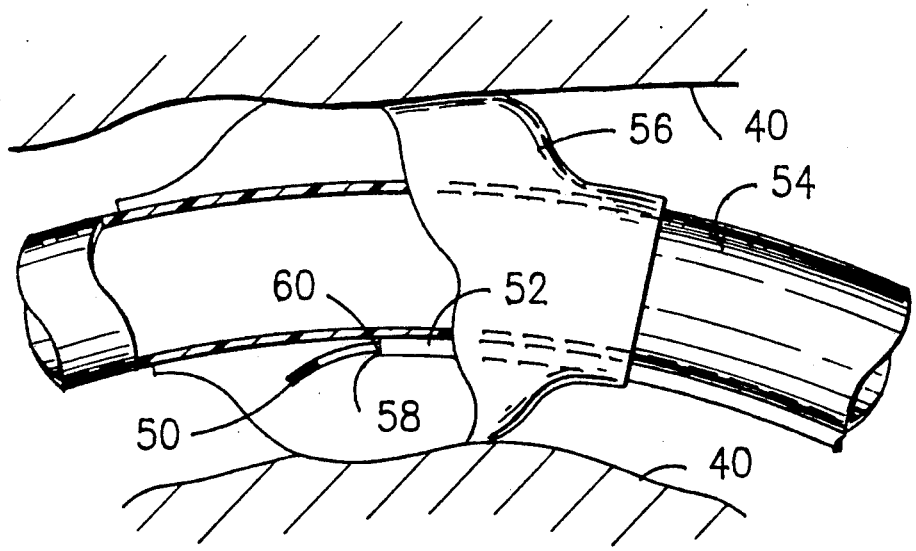
FIG. 3 is a further enlarged partially cut away and sectional view of a portion of the endotracheal tube and inflatable cuff as shown in FIG. 2, showing an alternative embodiment of the sound pressure level sensing means and the lumen.

FIG. 3 shows an alternative embodiment of the invention with sound pressure level sensing means 50 being much smaller than the one disclosed in FIG. 2. The sound pressure level sensing means 50 is of a size such that it can be passed through lumen 52, thus allowing it to be installed into or removed from the cuff 56 at any time. Thus, during an operation, after the endotracheal tube 54 has been inserted into the trachea and the inflatable cuff 56 has been inflated, the sensing means 50 may be inserted into place. It is also removable from the cuff at any time during or after the operation. This allows sensing means 50 to be readily replaceable and also to be reusable for subsequent operations.

In order to install the sensing means 50 inside the cuff 56, it may be necessary to remove the coupling means from the proximal end of the lumen. This in turn would open the lumen, which would allow the cuff to deflate. A means for preventing the back flow of air from the inflated cuff may be added, such as that which is shown in the form of flexible end flap 58. Flap 58 is attached in fixed relation to the end portion 60 of lumen 52, and acts as a check valve to preclude air from travelling back through the lumen. Flap 58 is forced shut against the distal end 60 of lumen 52 by the increased air pressure inside the cuff.

When the sensing means 50 reaches the distal end of the lumen 52, it forces open the flexible end flap 58. This allows a small volume of air contained inside the cuff to escape. The loss of this small volume of air does not affect the operation of the device. After the sensing means 50 has been fully inserted into the cuff, a plugging means (not shown) is inserted into the proximal end of the lumen 52. This plugging means acts to trap the wires in a secured relation to the lumen, thus helping to fix the location of the sensing means 50. The plugging means can also act as a strain relief, which prevents the wires from being forcibly removed from the sensing means 50, in case the wires are pulled excessively. Indeed, before the plugging means is installed, and if necessary, some additional pressurizing air may be passed down the lumen 52 past the wires of the sensing means 50. Alternatively, a "Y" connector may be installed at the proximal end of the lumen 52 to permit the passing of both the sensing means and its trailing wires, as well as inflating air for the cuff, down the lumen 52.

Another configuration of an endotracheal tube and inflated cuff assembly is depicted in FIG. 4, which shows an apparatus adapted for electrical stimulation of the heart muscle. The stimulation, known as pacing, is used to artificially control the heartbeat. The use of pacing is necessary when a patient's heartbeat is nonexistent, irregular, or occurring at a rate that is too slow.

Atrial pacing involves the insertion of a bipolar electrode, with poles being separated by a few centimeters, into the patient's trachea. The electrode poles contact the walls of the trachea and thus enable electrical pulses to be introduced to the body near the heart. These pulses are conducted to the heart, thus stimulating it.

Minimum power consumption is desired for medical safety reasons and for minimizing the drain of the electrical power supply. This minimum power consumption is realized through the proper adjustment of both the pulse duration and the amount of current flow. A typical pulse duration is around five to ten milliseconds and a typical amount of current flow is around ten to twenty milliamps.

There is an optimal location for minimizing the amount of power required for proper heart stimulation. The general area of the location can be reached on the initial insertion and placement of the electrodes. The actual optimal location can be realized by iteratively adjusting the location of the electrode. Such adjustments may not be possible in emergency situations.

A pair of wires 102 which are conductively coupled to electrodes 104 extend from lumen 100. These electrodes 104 perforate cuff 106 and are installed in a hermetically sealed relation thereto. The distance between the centers of the electrodes is in the order of 2 to 3 centimeters. The wires 102 must be flexible to accommodate both the inflated and deflated states of the cuff 106 and must be capable of carrying a current in the order of 10 to 20 milliamps.

Another embodiment of the invention, not shown in the drawings, includes an endotracheal tube with three lumens. One of the lumens could be used for inflation of an inflated cuff. The other lumens could be used for insertion of appropriate medical monitoring instrumentation.

Figure 5:
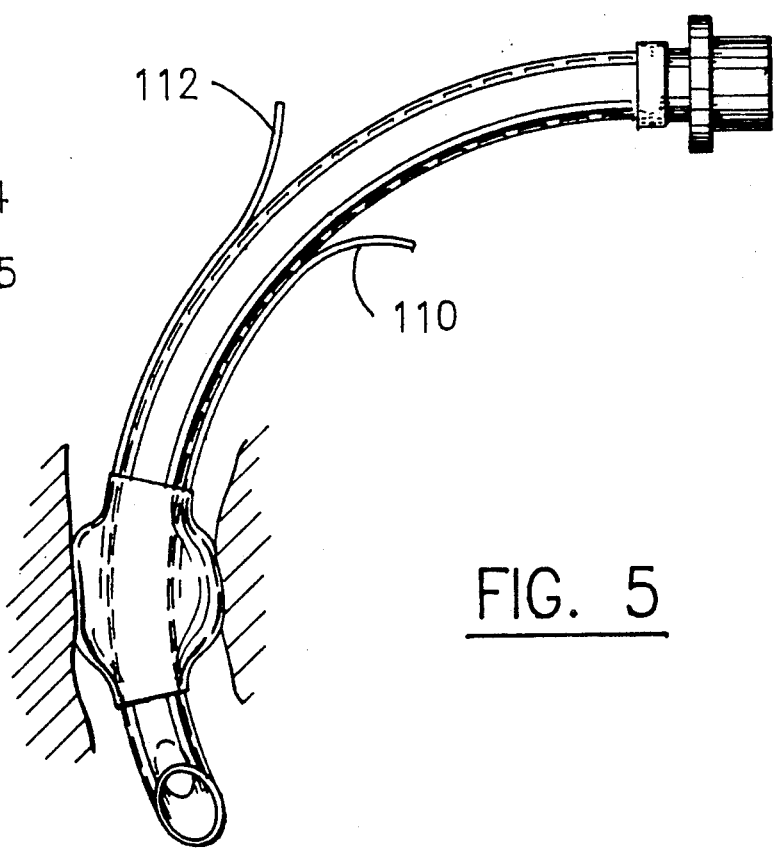
FIG. 5 is a side view, partially in cross section, of the endotracheal tube similar to that shown in FIG. 1, showing an alternative embodiment of the cuff inflated within the trachea.

FIG. 5 shows an alternative embodiment of the present invention in which the tube and cuff assembly has a first lumen 110 and a second lumen 112. Both the first and second lumens 110 and 112 are open at their distal ends to the interior of the inflatable cuff. The proximal end of the first lumen 110 is adapted to interface with means for inflating the cuff. The proximal end of the second lumen 112 is adapted to receive various medical instrumentation for insertion into the cuff.

It should be understood that the measurement of a person's heart rate is usually expressed as the number of beats per minute. Determination of this value, however, is not best done by counting the number of beats over a given period of time. This method would provide a heart rate value that is averaged over a period of time being considered.

A more instantaneous and more accurate way to effect heart rate measurement is to make use of the periodicity of the heartbeat. This is done by measuring the time between corresponding points, such as the start, of two consecutive heartbeats. This would produce a value expressed as the amount of time per beat (typically measured in seconds). The reciprocal of this number can subsequently be calculated in order to provide the number of heartbeats per unit time, with the appropriate conversion applied to express the value in beats per minute. This method is typically employed in medical equipment used in operating rooms.

The heart rate determined by using this periodic method is a very accurate representation. It represents the exact heart rate at the time of determination, and is not affected by the value of the heart rate prior to the period of time during which the measurement takes place. Any variation in heart rate from one period to another would, therefore, be immediately apparent. It is, of course, possible to apply mathematical techniques in order to also provide an average value for heart rate, if required.

Another embodiment of the present invention pertains to the use of an echo probe, such as that used in the Lawrence 3000 (TM) continuous cardiac output monitor, installed inside the cuff in a manner similar to the aforementioned medical instrumentation. This echo probe consists of a pair of ultrasonic crystals for the purpose of emitting and receiving ultrasonic signals. These signals, or a portion thereof, reach the aorta, and any changes of blood flow therein will cause a doppler shift in the frequency of the echoed ultrasonic signals, thus ultimately allowing an auditory reproduction of the heartbeat, or some other type of representation, to be constructed.

Yet another embodiment of the present invention includes means for determining the internal temperature of the patient during surgery, in the form of a temperature sensing probe, placed within the cuff. This probe can either be permanently installed during manufacture or could be small enough to be installable and removable during surgery, via one of the lumens. It could be coupled to an external monitor by electrical conductors or its signals could be transmitted over a radio frequency. The reason that the patient's temperature can be monitored from inside an inflatable cuff is that the air inside the cuff is at the same temperature as the surrounding tissue of the patient's body during surgery. In this manner, the patient's temperature can be monitored and measured accurately without the introduction of additional invasive medical equipment into the patient's body.

Another useful function of this endotracheal tube with internal sensor is that the monitoring functions of a cardiac probe can be duplicated. A cardiac probe is normally placed directly on the heart during surgery to monitor the heartbeat and heart sounds. Using some form of endotracheal sensor in place of a cardiac probe is advantageous for two reasons. Firstly, there is no longer an instrument introduced to the immediate heart area during surgery. Secondly, there is a possibility that the sensor may remain sterile, thus potentially allowing the sensor to be reusable.

As this disclosure indicates, the types of instrumentation that could be inserted into the second or third lumen are limited only by the imagination of the physician. For example, a low pressure gauge, and appropriate wires or radio frequency transmitting means could be inserted into the cuff as well. For purposes of this disclosure, the illustration of sensing means 42 or 50, and related parts, could also be understood as an illustration of this low pressure sensing means as well. The low pressure gauge could also be provided in regular and small sizes; the small size would be insertable in the same manner as sensing means 50. There are about 5-25 cubic centimeters of air in the cuff; the pressures in the cuff range from about 30 to 100 millimeters of mercury therein. Accordingly, a low pressure gauge capable of measuring such low pressures could be provided and an embodiment of this invention including such a low pressure gauge, or other cuff-condition-monitoring device, is within the scope of this invention. An analog or digital display of the cuff pressures or other conditions monitored would be provided to a suitable external monitor to convey the detected information to the physician.

FIG. 7 depicts lumen 32 secured to tube 20 by a suitable tape means 33, as mentioned hereinabove. In the embodiment of FIG. 7, lumen 32, which has an inner diameter of at least 1.0 millimeter, contains no sensing means other than the gaseous fluid therewithin. In this manner, lumen 32 carries acoustical signals to the physician that may be interpreted and acted upon. Thus, any distortion of signals that may result from the inherent limitations of electromechanical or other devices is avoided.

All embodiments of the present invention provide instantaneous information to the anesthesiologist. It has been discovered that the novel device reports life-threatening conditions to the anesthesiologist about 10 minutes before such conditions are reported by an EKG machine, for example. Obviously, the ability of the inventive device to provide early warning of important conditions has immeasurable value.

Industrial Applicability

This invention has applicability in the health care industry and is of particular importance to surgeons, anesthesiologists, and their patients.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An endotracheal heartbeat monitoring apparatus comprising:
   a flexible endotracheal tube for insertion through the mouth of a patient, said tube having a proximal end and a distal end;
   means defining a respiratory passage within the endotracheal tube for the control and monitoring of respiration during surgery;
   an inflatable cuff disposed near the distal end of the endotracheal tube, said cuff having proximal and distal ends;
   the proximal and distal ends of the cuff both being sealed to an outer surface of the endotracheal tube;
   said inflatable cuff being of appropriate size when deflated to pass easily through the trachea, and of approximate size when inflated to contact and conform intimately to the inner wall of the trachea;
   at least one flexible lumen disposed lengthwise along the endotracheal tube from said proximal end thereof to the interior of said inflatable cuff;

said at least one lumen being disposed outside of said endotracheal tube in contacting relation to said endotracheal tube;

echo probe means within the inflatable cuff for the purpose of sensing changes in the ultrasonic sound level pressures within the cuff, and for producing a signal in response to these changes; and transmission means for transmitting said signal to a monitoring device external to said apparatus.

2. The endotracheal heartbeat monitoring apparatus of claim 1, wherein the echo probe means includes ultrasonic crystals.

3. The endotracheal heartbeat monitoring apparatus of claim 1, wherein there is a first lumen and a second lumen and wherein each of said first and second lumens have respective inner diameters no less than 1.0 mm.

4. The endotracheal heartbeat monitoring apparatus of claim 3, further comprising means for permitting inflation of said cuff, said first lumen being said means permitting inflation, and further comprising means permitting passage of electrically conductive wires into said cuff, said second lumen being said means permitting passage.

5. The endotracheal heartbeat monitoring apparatus of claim 1, wherein said echo probe means is fixedly installed within said inflatable cuff.

6. The endotracheal heartbeat monitoring apparatus of claim 1, wherein said echo probe means is removably installed within said inflatable cuff.

7. The endotracheal heartbeat monitoring apparatus of claim 1, further comprising means for permitting fluid communication with the interior of said inflatable cuff, said means for permitting said fluid communication being said at least one lumen.

8. The endotracheal heartbeat monitoring apparatus of claim 7, wherein means associated with said at least one lumen substantially precludes fluid flow in an outward direction from said inflatable cuff.

9. The endotracheal heartbeat monitoring apparatus of claim 7, further comprising means permitting insertion of said echo probe means into the interior of said inflatable cuff, said means for permitting said insertion being said at least one lumen.

10. The endotracheal heartbeat monitoring apparatus of claim 7, further comprising means permitting removal of said echo probe means from the interior of said inflatable, said means for permitting said removal being said at least one lumen.

11. The endotracheal heartbeat monitoring apparatus of claim 1, wherein said at least one lumen has an inner diameter of at least 1.0 mm.

12. The endotracheal heartbeat monitoring apparatus of claim 1, wherein a low pressure sensing means is conductively coupled to a self-contained radio frequency emitting device and wherein said low pressure sensing means is positioned within said inflatable cuff.

* * * * *